United States Patent
Nikitin et al.

(10) Patent No.: US 11,578,965 B2
(45) Date of Patent: Feb. 14, 2023

(54) COST-EFFECTIVE LINE-SCAN OPTICAL COHERENCE TOMOGRAPHY APPARATUS

(71) Applicant: Hong Kong Applied Science and Technology Research Institute Company Limited, Hong Kong (CN)

(72) Inventors: Vladislav Nikitin, Hong Kong (CN); Pingping Feng, Hong Kong (CN); Ka Shing Anthony Yuen, Hong Kong (CN); Sifan Xie, Guangzhou (CN); Xinliang Li, Hong Kong (CN)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 0 days.

(21) Appl. No.: 17/303,286

(22) Filed: May 26, 2021

(65) Prior Publication Data

US 2022/0381551 A1    Dec. 1, 2022

(51) Int. Cl.
  *G01B 9/02*  (2022.01)
  *G01B 9/02091*  (2022.01)
  *A61B 5/00*  (2006.01)

(52) U.S. Cl.
  CPC ........ *G01B 9/02091* (2013.01); *A61B 5/0066* (2013.01); *G01B 9/02035* (2013.01)

(58) Field of Classification Search
  CPC .............. G01B 9/02091; G01B 9/0209; G01B 9/0235; A61B 5/0066
  See application file for complete search history.

(56) References Cited

U.S. PATENT DOCUMENTS 6,650,413 B2    11/2003    Thibault et al.
8,593,640 B2    11/2013    Kim et al.
(Continued)

FOREIGN PATENT DOCUMENTS

CN    101889188 A    11/2010
CN    105324649 A    2/2016
(Continued)

OTHER PUBLICATIONS

Benefits of Structured Light Laser vs Laser Line Generator, Sep. 2020, https://web.archive.org/web/20200929200430/https://www.prophotonix.com/blog/benefits-structured-light-laser-vs-laser-line-generator/ (Year: 2020).*

(Continued)

*Primary Examiner* — Tarifur R Chowdhury
*Assistant Examiner* — Jonathon Cook
(74) *Attorney, Agent, or Firm* — S&F/WEHRW

(57) ABSTRACT

An implementation cost of a line-scan optical coherence tomography (OCT) apparatus is reduced by miniaturizing a scanning mirror and using a light source with relaxed requirement in intensity uniformity. The mirror reflects a probe light beam to different parts of a sample for line-scanning the sample. A line-compressing lens compresses the probe light beam's cross-sectional length before the beam reaches the mirror, allowing the mirror to be miniaturized to reflect only the compressed beam. In generating a linear light beam that gives the probe light beam, a cascade of collimating lens, Powell lens and focusing lens generates the linear light beam from a raw light beam of a point source. A slit further filters the linear light beam to remove a peripheral portion thereof such that the linear light beam is substantially uniform in intensity even if an asymmetrical divergent light source is used.

17 Claims, 8 Drawing Sheets

(56) References Cited

U.S. PATENT DOCUMENTS

| | | | |
|---|---|---|---|
| 9,816,803 B2 | 11/2017 | Kulkarni | |
| 2014/0028974 A1* | 1/2014 | Tumlinson | G01B 9/02047 356/457 |
| 2020/0201058 A1 | 6/2020 | Ginner et al. | |
| 2020/0245905 A1 | 8/2020 | Chen et al. | |

FOREIGN PATENT DOCUMENTS

| | | |
|---|---|---|
| CN | 110178069 A | 8/2019 |
| WO | 2018/203506 A1 | 11/2018 |
| WO | 2019/035441 A1 | 2/2019 |

OTHER PUBLICATIONS

Yoshifumi Nakamura, Shuichi Makita, Masahiro Yamanari, Masahide Itoh, Toyohiko Yatagai, and Yoshiaki Yasuno, "High-speed three-dimensional human retinal imaging by line-field spectral domain optical coherence tomography," Opt. Express 15, 7103-7116 (2007) (Year: 2007).*

J. Wang, C. Dainty, and A. Podoleanu, "Line-field Spectral Domain Optical Coherence Tomography using a 2D Camera," in Optical Coherence Tomography and Coherence Techniques IV, P. Anderson and B. Bouma, eds., vol. 7372 of Proceedings of SPIE-OSA Biomedical Optics, paper 7372_21 (Year: 2009).*

R. Haindl, W. Trasischker, B. Baumann, M. Pircher & O.K. Hitzenberger (2015) Three-beam Doppler optical coherence tomography using a facet prism telescope and MEMS mirror for improved transversal resolution, Journal of Modern Optics, 62:21, 1781-1788, DOI: 10.1080/09500340.2014.983569 (Year: 2014).*

Eppig, Timo & Rubly, Kathrin & Eissel, Antonia & Langenbucher, Achim. (2019). Visualization of Light Propagation with Multifocal Intraocular Lenses Using the Ouzo Effect. BioMed Research International. 2019. 1-10. 10.1155/2019/6425040. (Year: 2019).*

International Search Report and Written Opinion of PCT application No. PCT/CN2021/098472 issued from the International Search Authority dated Jan. 26, 2022.

N. Yoshifumi, M. Shuichi, Y. Masahiro, I. Masahide, Y. Toyohiko, and Y. Yoshiaki, "High-speed three-dimensional human retinal imaging by line-field spectral domain optical coherence tomography," Optics Express, vol. 15, No. 12, pp. 7103-7116, Jun. 2007.

Z. Al-Qazwini, Z. Y. G. Ko, K. Mehta, and N. Chen, "Ultrahigh-speed line-scan SD-OCT for four-dimensional in vivo imaging of small animal models," Biomedical Optics Express, vol. 9, No. 3, pp. 1216-1227, Mar. 2018.

A. F. Zuluaga and R. Richards-Kortum, "Spatially resolved spectral interferometry for determination of subsurface structure," Optics Letters, vol. 24, pp. 519-521, May 1999.

A. B. Vakhtin, K. A. Peterson, W. R. Wood, and D. J. Kane, "Differential spectral interferometry: an imaging technique for biomedical applications," Optics Letters, vol. 28, pp. 1332-1334, Aug. 2003.

A. F, Fercher, W. Drexler, C. K. Hitzenberger and T. Lasser, "Optical coherence tomography—principles and applications," Reports on Progress in Physics, vol. 66, pp. 239-303, Feb. 2003.

\* cited by examiner

COST-EFFECTIVE LINE-SCAN OPTICAL COHERENCE TOMOGRAPHY APPARATUS

LIST OF ABBREVIATIONS

2D Two-dimensional
IR Infrared
MEMS Microelectromechanical system
MTF Modulation transfer function
OCT Optical coherence tomography

FIELD OF THE INVENTION

The present disclosure generally relates to an apparatus for imaging a sample by OCT using line scanning. In particular, the present disclosure relates to such apparatus implemented with a miniaturized mirror for controlling line scanning of the sample while allowing a manufacturing cost of the apparatus to be reduced.

BACKGROUND

OCT is an optical technique for cross-sectionally imaging a sample with a micrometer-scale axial resolution. This technique has found applications in non-invasive medical imaging, and in particular, in retinal imaging. In scanning a sample by OCT, both raster scanning (point-by-point scanning) and line scanning may be used. The line-scanning technique is of greater interest due to its higher speed in scanning the sample over the raster-scanning technique, although an OCT device using line scanning (hereinafter referred to as a line-scan OCT device) is more complex to implement and is hence more costly. It is desirable to reduce an implementation cost of the line-scan OCT device.

One factor leading to a high implementation cost is that a large scanning galvanometer mirror is usually used in the line-scan OCT device for directing a linear light beam to illuminate different parts of the sample, e.g., in OCT devices disclosed in US 2020/0201058, in N. YOSHIFUMI et al., "High-speed three-dimensional human retinal imaging by line-field spectral domain optical coherence tomography," *Optics Express*, vol. 15, no. 12, pp. 7103-7116, June 2007, and in Z. AL-QAZWINI et al., "Ultrahigh-speed line-scan SD-OCT for four-dimensional in vivo imaging of small animal models," *Biomedical Optics Express*, vol. 9, no. 3, pp. 1216-1227, March 2018. Electronic control of steering a large mirror is very complex and expensive, no matter the used principle. It is desirable if the size of scanning galvanometer (or any other type) mirror can be reduced for reducing the implementation cost.

Another factor is that a light source having a high uniformity in power intensity is desirable in realizing the line-scan OCT device in order to ensure high-quality accurate measurement of the sample. Such light source is expensive. To reduce the implementation cost, it is desirable if a relaxed requirement in intensity uniformity can be applied to the light source while achieving a high uniformity in power intensity of a linear light beam for probing the sample is realizable from the light source by using an optical technique.

There is a need in the art for a cost-effective line-scan OCT device that achieves reducing a size of scanning galvanometer (or any other) mirror and/or using a light source with a relaxed requirement in intensity uniformity.

SUMMARY OF THE INVENTION

An aspect of the present disclosure is to provide an apparatus for imaging a sample by OCT. The apparatus provides an advantage that an implementation cost is reducible by miniaturizing a scanning mirror and/or using a light source with a relaxed requirement in intensity uniformity.

The apparatus comprises a line generator, a beam splitter, a telescope, a mirror and a line-compression lens. The line generator is used for generating a linear light beam. The beam splitter is configured to split the linear light beam into a reference light beam and a probe light beam. The probe light beam is arranged to travel from the beam splitter to the sample over a sample path for line-scanning the sample to thereby cause the sample to generate a backscattered light beam. The sample path allows the backscattered light beam to be transmitted to the beam splitter. The reference light beam is arranged to travel along a reference path and return to the beam splitter. The beam splitter is further configured to combine the returned reference light beam and the backscattered light beam to form an optical interference signal for analysis to thereby yield tomographical information of the sample. The telescope, the mirror and the line-compression lens are located on the sample path. The telescope is configured to project the probe light beam to the sample and capture the backscattered light beam. The mirror is used for reflecting the probe light beam exited from the beam splitter to the telescope and reflecting the backscattered light beam exited from the telescope to the beam splitter. In addition, the mirror is a scanning galvanometer (or any other) mirror, which is controllably steerable so as to steer the probe light beam to different parts of the sample in line-scanning the sample. The line-compression lens is positioned between the beam splitter and the mirror. The line-compression lens is configured to compress a cross-sectional length of the probe light beam from a first length to a shorter, second length when the probe light beam reaches the mirror, thereby allowing the mirror to be miniaturized to reflect only the probe light beam compressed with a shorter cross-sectional length.

The line-compression lens may further be configured to keep a cross-sectional width of the probe light beam substantially unchanged over the sample path between the line-compression lens and the mirror.

In certain embodiments, the line generator comprises a light source, a first collimating lens, a Powell lens and a first focusing lens. The light source is used for emitting a raw light beam. The first collimating lens is used for generating a first collimated light beam from the raw light beam. The Powell lens is used for generating a diverging line of light from the first collimated light beam. The first focusing lens is used for generating the linear light beam from the diverging light line. A cascade of the first collimating lens, the Powell lens and the first focusing lens allows a point source to be used as the light source in generating the linear light beam, and enables the first collimating light beam to expand in cross-sectional length for providing a predetermined cross-sectional length required by the linear light beam.

In certain embodiments, a distance between the Powell lens and the first focusing lens is adjustable, allowing a cross-sectional length of the linear light beam to be controllably adjustable for precise alignment.

Preferably, the apparatus further comprises a first slit located between the line generator and the beam splitter for filtering the linear light beam before reaching the beam splitter such that a peripheral portion of the linear light beam emitted from the line generator is filtered off. It thereby allows the linear light beam after filtering to be substantially uniform in intensity even if an asymmetrical divergent light source is used as the light source.

In certain embodiments, the mirror is a MEMS mirror.

In certain embodiments, the apparatus further comprises a reference channel configured to receive the reference light beam exited from the beam splitter, allow the reference light beam to travel on a first half of the reference path, form the returned reference light beam by reflecting the reference light beam, allow the returned reference light beam to travel on a second half of the reference path, and direct the returned reference light beam to the beam splitter after traveling on the second half of the reference path is completed.

In certain embodiments, the apparatus further comprises a reference-path mirror and an actuator. The reference-path mirror is installed at an end of the reference channel for reflecting the reference light beam so as to form the returned reference light beam that travels back to the beam splitter. The actuator is attached to the reference-path mirror for fine-tuning an optical path length of the reference path.

In certain embodiments, the actuator is a piezoelectric actuator.

Preferably, the apparatus further comprises a linear spectrometer for spectrally measuring the optical interference signal to thereby yield tomographical information of the sample.

In certain embodiments, the apparatus further comprises a second slit located between the beam splitter and the linear spectrometer for rejecting unwanted light components from the optical interference signal before the optical interference signal is received by the linear spectrometer.

In certain embodiments, the linear spectrometer comprises a second focusing lens, a diffraction grating, a third focusing lens and a 2D photosensor. The diffraction grating is used for diffracting the optical interference signal so as to disperse the optical interference signal into spectra to thereby form a spectral image. The spectral image contains a distribution of dispersed spectra. The second focusing lens is used for receiving the optical interference signal from outside the linear spectrometer and projecting the received optical interference signal to the diffraction grating. A 2D photosensor is used for imaging the spectral image to obtain the distribution of dispersed spectra. The third focusing lens, positioned between the diffraction grating and the 2D photosensor, is used for projecting the spectral image onto the 2D photosensor.

In certain embodiments, the beam splitter is a cube beam splitter or a plate beam splitter.

In certain embodiments, the telescope comprises a first telescope lens and a second telescope lens arranged in a serial cascade.

In certain embodiments, the first telescope lens, the second telescope lens, or both, are adjustable in optical power for accurately projecting the probe light beam on the sample.

Other aspects of the present disclosure are disclosed as illustrated by the embodiments hereinafter.

Figure 1:
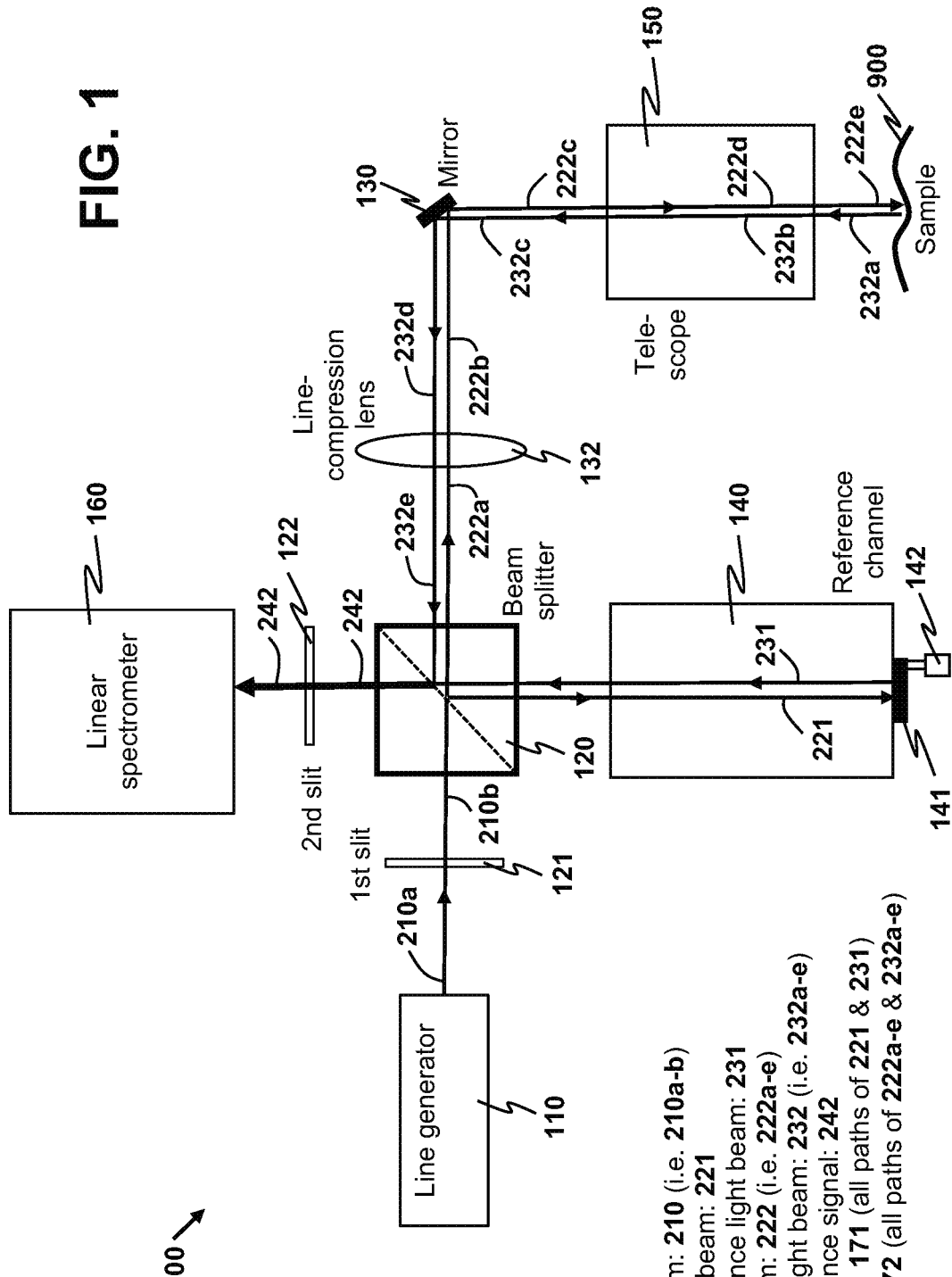
FIG. 1 depicts a schematic diagram of an apparatus for imaging a sample by OCT in accordance with an exemplary embodiment of the present disclosure.

Skilled artisans will appreciate that elements in the figures are illustrated for simplicity and clarity and have not necessarily been depicted to scale.

DETAILED DESCRIPTION

As used herein, "a linear light beam" is a light beam whose cross-section has a shape of a straight line, where the cross-section is perpendicular to the light beam's propagation direction. The cross-section has "a cross-sectional length" and "a cross-sectional width" where the cross-sectional length is longer than the cross-sectional width. Usually, the cross-sectional width is considered negligible in comparison to the cross-sectional length. For example, a linear light beam usable in OCT for line-scanning a human retina may have a cross-sectional width as low as a few micrometers but a cross-sectional length of a few millimeters or more.

As used herein, "a beam size" of a light beam is the largest one-dimensional length between any two points on a periphery of a cross-section of the light beam, where the cross-section is perpendicular to the light beam's propagation direction. Note that the cross-sectional length of a linear light beam is upper bounded by the beam size of the linear light beam. For a linear light beam with a cross-sectional width negligible in comparison to a cross-sectional length, the cross-sectional length is closely approximated by the beam size of the linear light beam. If a first linear light beam is compressed by an optical device into a second linear light beam close to a light spot, it is practically more convenient to measure sizes of the first and second linear light beams in term of beam size than in term of cross-sectional length.

Disclosed herein is an apparatus for imaging a sample by OCT. The apparatus uses line scanning in scanning the sample so that the apparatus is a line-scan OCT device. In particular, the apparatus, through different embodiments thereof, provide various advantages, which includes reducing a size of a scanning mirror and allowing a light source with a relaxed requirement in power-intensity uniformity to be used. These advantages allow an implementation cost of the disclosed apparatus to be reducible.

Although the disclosed apparatus is useful for medical imaging applications and in particular, retinal imaging applications, the present disclosure is not limited to medical imaging applications; the disclosed apparatus is also usable for non-medical imaging applications such as cross-sectional imaging of multilayer optical disks.

As mentioned above, US 2020/0201058, N. YOSHIFUMI et al. and Z. AL-QAZWINI et al. have disclosed different line-scan OCT devices each using a large scanning mirror for directing a probe light beam to a sample. In each of the OCT devices of N. YOSHIFUMI et al. and Z. AL-QAZWINI et al., the probe light beam is focused on the sample by a focusing lens as the last stage of optically processing the probe light beam. Furthermore, the focusing lens is used to shape the probe light beam as a linear light beam from a broad light beam, whose cross-sectional length and cross-sectional width are comparable. A scanning mirror is used to controllably direct the broad light beam to the focusing lens with a selected angle of incidence on the focusing lens. The large cross-sectional area of the broad light beam requires the scanning mirror to have a large size in area. The line-scan OCT device of US 2020/0201058, on the other hand, generates a linear light beam from a light source such that a scanning mirror receives the linear light beam for reflection. The cross-sectional width of the linear light beam is negligible such that the cross-sectional width is not a factor of demanding a large mirror. However, the cross-sectional length is still sizable and demands the mirror to be of large size. Based on the foregoing observations, the Inventors identify that a scanning mirror can be reduced in size if the mirror receives a linear light beam for reflection and if the linear light beam has a reduced cross-sectional length. These two findings are used in the development of the disclosed apparatus, as elaborated as follows.

The disclosed apparatus is exemplarily illustrated with the aid of FIG. 1. FIG. 1 depicts a schematic diagram of an exemplary line-scan OCT apparatus 100 used for imaging a sample 900.

In the apparatus 100, a line generator 110 is used to generate a linear light beam 210 for probing the sample 900. (In FIG. 1, the linear light beam 210 is shown as a concatenation of light-beam segments 210a-b.) In retinal imaging applications using line-scan OCT, for instance, a micrometer-scale resolution is usually demanded in imaging a retina. The cross-sectional width of the linear light beam 210 is usually in the order of micrometers whereas the cross-sectional length thereof is in the order of millimeters. The linear light beam 210 is usually narrow in most practical situations. In addition, one requirement of carrying out OCT is that the linear light beam 210 has a low time coherence. That is, the linear light beam 210 has a broad spectrum. Furthermore, since absorption of most human tissues tends to decrease with increasing wavelength, the linear light beam 210 is usually selected to be IR in medical line-scan OCT applications. The linear light beam 210 generated by the line generator 110 is usually a collimated beam, although slight divergence or convergence may be present in the linear light beam 210 if tolerable or if intended.

The linear light beam 210 is received by a beam splitter 120. The beam splitter 120 is configured to split the linear light beam 210 into a reference light beam 221 and a probe light beam 222. Preferably, the reference light beam 221 and the probe light beam 222 have the same power level or nearly the same power level. The reference light beam 221 and the probe light beam 222 travel in two different directions. (In FIG. 1, the probe light beam 222 is shown as a concatenation of light-beam segments 222a-e.) The probe light beam 222 exited from the beam splitter 120 is arranged to (forwardly) travel from the beam splitter 120 to the sample 900 over a sample path 172 (depicted as a concatenation of path segments 222a-e and 232a-e in FIG. 1) for line-scanning the sample 900. During traveling to the sample 900, the probe light beam 222 is processed by various optical components on the sample path 172 for reflecting, focusing and guiding the probe light beam 222. Upon irradiated by the probe light beam 222, the sample 900 generates a backscattered light beam 232. The sample path 172 allows the backscattered light beam 232 to (backwardly) travel from the sample 900 to the beam splitter 120. The reference light beam 221 exited from the beam splitter 120 is arranged to travel along a reference path 171 (depicted as a concatenation of path segments 221 and 231 in FIG. 1) and return to the beam splitter 120 as a returned reference light beam 231. The beam splitter 120 is further configured to combine the returned reference light beam 231 and the backscattered light beam 232 to form an optical interference signal 242 for analysis to thereby yield tomographical information of the sample 900.

In the apparatus 100, a line-compression lens 132, a mirror 130 and a telescope 150 are installed on the sample path 172 for optically handling the probe light beam 222 before the probe light beam 222 is irradiated on the sample 900. These optical components 132, 130, 150 are also used to optically handle the backscattered light beam 232 during transmission from the sample 900 to the beam splitter 120.

The telescope 150 is an optical device arranged to be in proximity to the sample 900. The telescope 150 is configured to project the probe light beam 222e to the sample 900 and capture the backscattered light beam 232a emitted from the sample 900.

The mirror 130 is used for reflecting the probe light beam 222d exited from the line-compression lens 132 to the telescope 150. In addition, the mirror 130 is used for reflecting the backscattered light beam 232c exited from the telescope 150 to the line-compression lens 132. The mirror 130 is also a scanning mirror. Particularly, the mirror 130 is controllably steerable so as to steer the probe light beam 222c-e to different parts of the sample 900 in line-scanning the sample 900. The mirror 130 that is steerable may be implemented as a rotatable mirror about a single axis or multiple axes.

Figure 2:
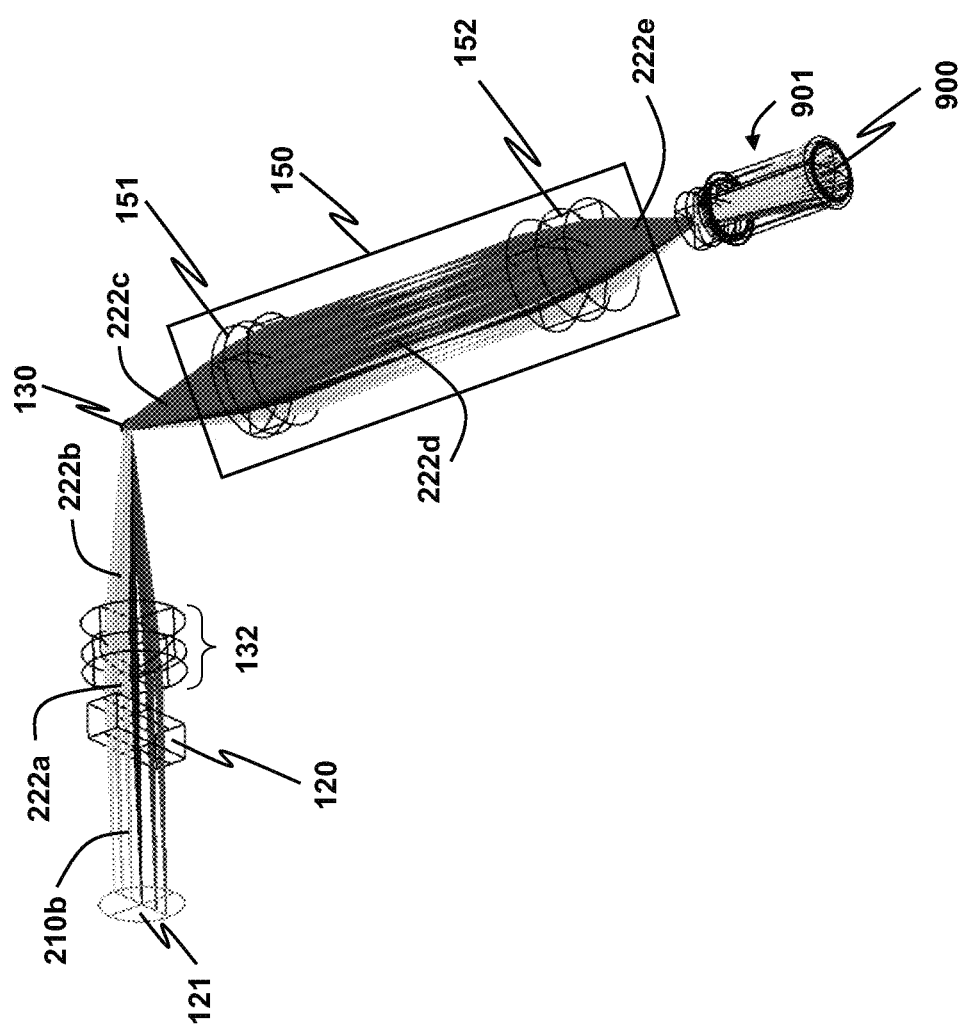
FIG. 2 depicts a ray-tracing diagram of a part of the apparatus where a probe light beam is traveled on a sample path from a beam splitter to the sample, illustrating an advantage of miniaturizing a scanning galvanometer (or any other) mirror by compressing the probe light beam.
Figure 3:
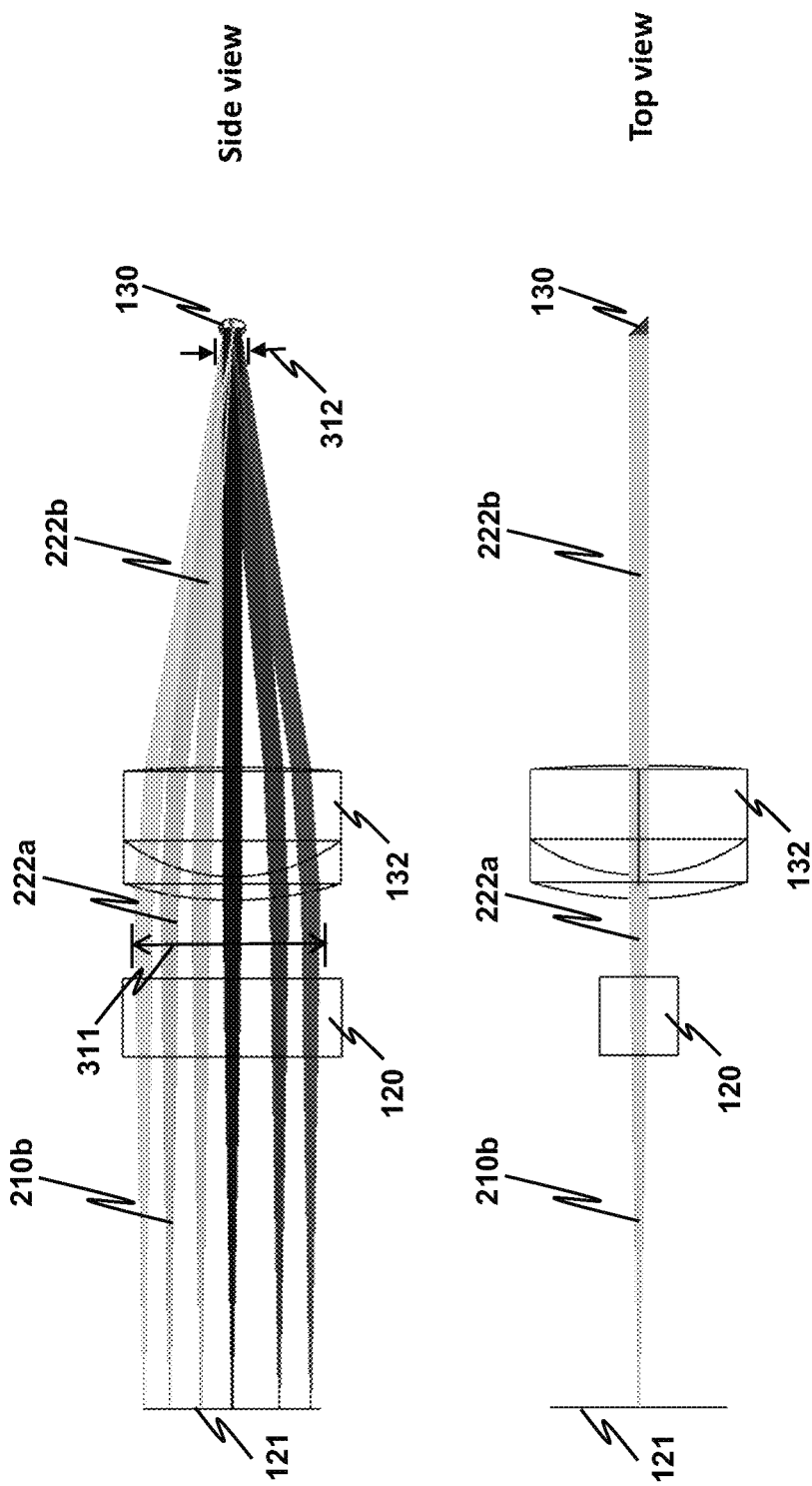
FIG. 3 depicts a side view and a top view of the ray-tracing diagram of FIG. 2 for a portion of the sample path between the beam splitter and the mirror, showing a compressive effect provided by a line-compression lens positioned between the beam splitter and the mirror in compressing the probe light beam.

Advantages of using the line-compression lens 132 on the sample path 172 are illustrated with the aid of FIGS. 2 and 3. FIG. 2 depicts a ray-tracing diagram showing the propagation of the probe light beam 222 along the sample path 172 from the beam splitter 120 to the sample 900. As an illustrative example, the sample 900 is a retina model housed in an eye model 901. FIG. 3 depicts a side view and a top view of the ray-tracing diagram for a portion of the sample path 172 between the beam splitter 120 and the mirror 130, showing a compression action taken by the line-compression lens 132.

Consider the portion of the sample path 172 on which the mirror 130 receives the probe light beam 222a exited from the beam splitter 120 via the line-compression lens 132. The probe light beam 222a exited from the beam splitter 120 is a collimated light beam having a cross-sectional length of, say, a first length 311. If the probe light beam 222a were to be directly received by the mirror 130 for reflection, the mirror 130 would be required to have a size (in length) at least the first length 311 multiplied by a multiplying factor. The multiplying factor takes into account an increased length in receiving the probe light beam 222b due to oblique incidence of the probe light beam 222b onto the mirror 130. Hence, the multiplying factor is greater than unity. The line-compression lens 132 is configured to compress the cross-sectional length of the probe light beam 222a from the first length 311 to a shorter, second length 312 when the probe light beam 222b reaches the mirror 130. The line-compression lens 132 is realizable as a focusing lens to converge the probe light beam 222a such that the cross-sectional length of the probe light beam 222b exited from the line-compression lens 132 diminishes from the first length 311 to the shorter, second length 312 over the course between the line-compression lens 132 and the mirror 130. Since the probe light beam 222b has a shorter cross-sectional length upon arrival at the mirror 130, the mirror 130 only needs to have a reduced size sufficient to accommodate the probe light beam 222b having the second length 312 in cross-sectional length. Most desirably, it is preferable that the probe light beam 222b is compressed to a small spot when reached the mirror 130. As a result, including the line-compression lens 132 on the sample path 172 advantageously allows the mirror 130 to be miniaturized to reflect only the probe light beam 222 compressed with the shorter cross-sectional length. Using a compact mirror as the scanning mirror (viz., the mirror 130) reduces complexity in electronic control of the mirror 130, thereby reducing an implementation cost of the apparatus 100. Other additional advantages of using the compact mirror include a lower weight of the mirror 130 and a smaller space requirement in accommodating the mirror 130 in the apparatus 100.

Note that the cross-sectional length of the probe light beam 222b is upper bounded by a beam size thereof. Therefore, ensuring that the cross-sectional length of the probe light beam 222b is reduced from the first length to the second length when the probe light beam 222b reaches the mirror 130 is experimentally verifiable by measuring the cross-sectional length of the probe light beam 222b exited from the line-compression lens 132 and the beam size of the probe light beam 222b that reaches the mirror 130. This experimental procedure is especially useful in testing the apparatus 100 if the probe light beam 222b is reduced to a small spot when reached the mirror 130.

As mentioned above, the cross-sectional length of the probe light beam 222b is closely approximated by the beam size, especially when the cross-sectional width of the probe light beam 222b is negligible in comparison to the cross-sectional length. It follows that instead of designing the line-compression lens 132 in terms of its cross-sectional length, the line-compression lens 132 may be designed such that the beam size of the probe light beam 222b is reduced from the first length to the second length. Since measuring the beam size is easier than measuring the cross-sectional length in experiments, and since it is most desirable to converge the probe light beam 222b to a small spot when reached the mirror 130, designing the line-compression lens 132 in terms of the beam size instead of the cross-sectional length provides an advantage that experimental verification or testing of the line-compression lens 132 is simplified.

Figure 4:
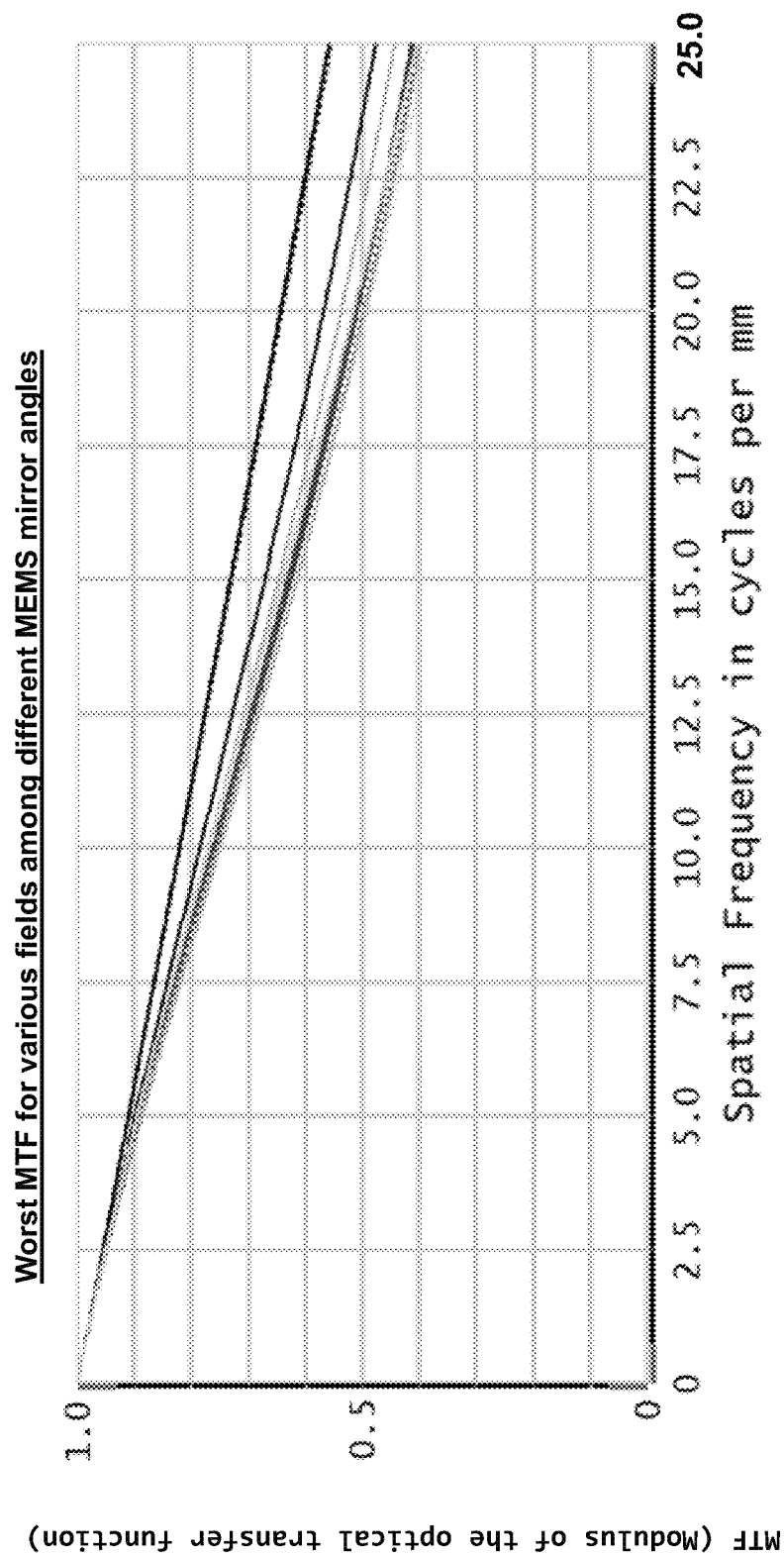
FIG. 4 depicts the worst MTF among different scanning angles for a single MEMS mirror used as the scanning mirror of the apparatus for demonstrating that using the MEMS mirror with a small size to reflect the compressed probe light beam (having a beam size as low as ~1 mm) still provides a spatial resolution sufficient for retinal OCT imaging with required angular scanning range.

One may concern that using a compact small-sized mirror to reflect the compressed probe light beam 222b potentially reduces a spatial resolution of using the probe light beam 222c exited from the mirror 130 in imaging the sample 900. Practically, the compact small-sized mirror may be a MEMS mirror. To analyze the spatial resolution supported by the MEMS mirror, simulation runs were performed for estimating the worst MTF for using a single MEMS mirror of less than 3 mm in size as the mirror 130 for projecting the probe light beam 222c with a beam size of ~1 mm onto the sample 900 (which was a retina model) via the telescope 150. FIG. 4 depicts the estimated worst MTF. It is apparent that the MTF is around 0.38 for a spatial frequency of 25 cycles per mm. It follows that 25 line pairs per mm of the probe light beam 222e can be used to image the sample 900, corresponding to an imaging resolution of 20 μm, which is generally sufficient for retinal OCT imaging. The analysis demonstrates that using the MEMS mirror with a small size less than 3 mm to reflect the compressed probe light beam 222c (having a beam size as low as ~1 mm) still provides a spatial resolution sufficient for retinal OCT imaging.

Since the cross-sectional width of the probe light beam 222a is considerably shorter than the cross-sectional length thereof, and since the line-compression lens 132 is primarily designed to compress the cross-sectional length of the probe light beam 222a, the radius of curvature of the line-compression lens 132 is most often not small enough to substantially increase the cross-sectional width of the probe light beam 222b when reached the mirror 130. See the top view depicted in FIG. 3. Nonetheless, it is preferable that the line-compression lens 132 is further configured to keep the cross-sectional width of the probe light beam 222b substantially unchanged over the sample path 172 between the line-compression lens 132 and the mirror 130.

Note that after the mirror 130 reflects the probe light beam 222b, the probe light beam 222c exited from the mirror 130 diverges, and expands in cross-sectional length during traveling to the telescope 150, effectively reversing a compression operation provided by the line-compression lens 132. Depending on different realizations of the apparatus 100, the cross-sectional length of the probe light beam 222c may or may not be the first length 311 (viz., the original cross-sectional length of the probe light beam 222a).

In certain embodiments, the telescope 150 is formed with a first telescope lens 151 and a second telescope lens 152 arranged in a serial cascade as shown in FIG. 2. The first telescope lens 151 is arranged to receive the probe light beam 222c after the cross-sectional length thereof is expanded. The first telescope lens 151 is a focusing lens used to refract the divergent probe light beam 222c to form the parallel-running probe light beam 222d. The latter probe light beam 222d travels along the telescope 150 to the second telescope lens 152. The second telescope lens 152 is another focusing lens to focus the probe light beam 222d towards the sample 900 such that the probe light beam 222e is irradiated on the sample 900.

Figure 5:
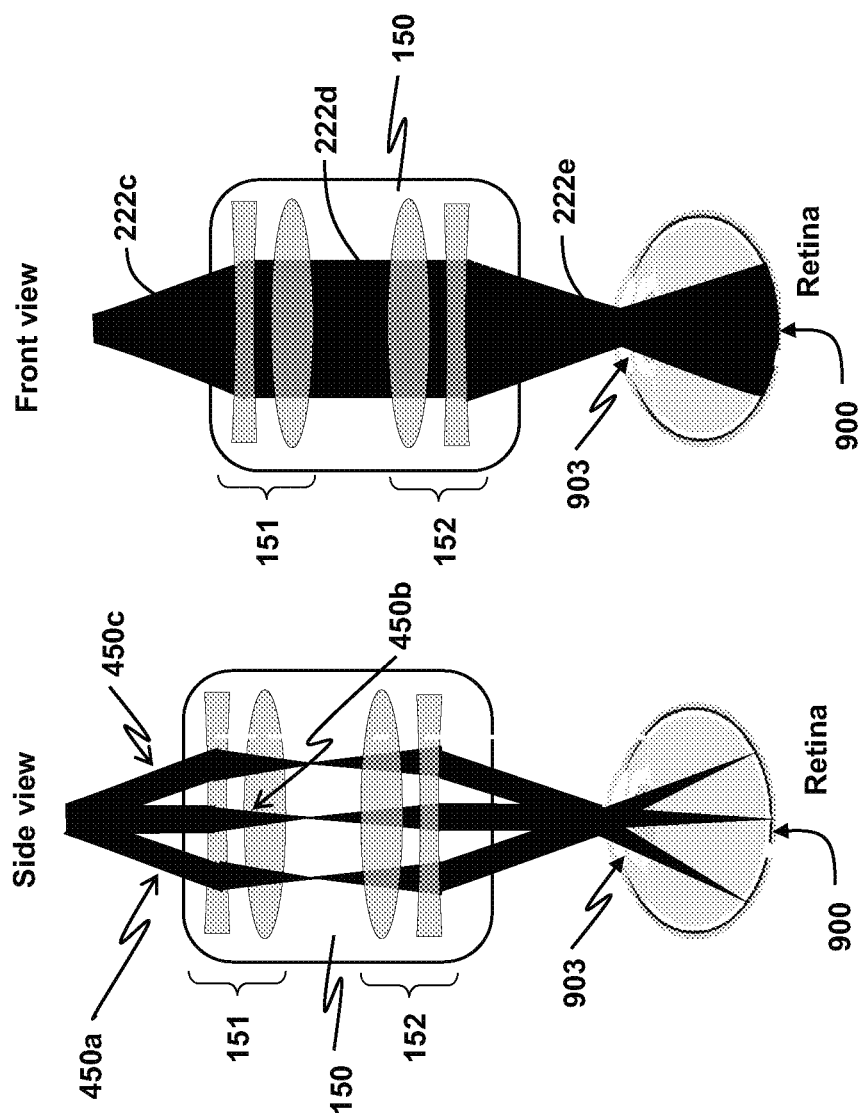
FIG. 5 depicts a side view and a front view of a telescope used in the disclosed apparatus for illustrating line scanning of the sample, which is a retina of an eye, over different parts of the retina.

FIG. 5 depicts a side view and a front view of the telescope 150 for illustrating line scanning of the sample 900 (a retina of an eye) over different parts of the retina 900. As an illustrative example shown in FIG. 5, the mirror 130 is controlled to set the probe light beam 222c-e into three different propagation paths 450a-c at three different time instants. When the probe light beam 222e travels from the second telescope lens 152 to the retina 900, the refractive power of the eye's crystalline lens 903 is required to be taken into account in accurately focusing the probe light beam 222e onto the retina 900.

Preferably, the telescope 150 is adjustable in optical power for accurately projecting the probe light beam 222e on the sample 900. Adjusting the optical power of the telescope 150 is realizable if one or both of the first and second telescope lenses 151, 152 are adjustable in optical power.

The optical transmission of the backscattered light beam 232 from the sample 900 back to the beam splitter 120 over the sample path 172 through the telescope 150, the mirror 130 and the line-compression lens 132 is reciprocal to the optical transmission of the probe light beam 222 from the beam splitter 120 to the sample 900. Those skilled in the art will appreciate that details regarding the former optical transmission can be derived according to the disclosure regarding the latter optical transmission.

Figure 6:
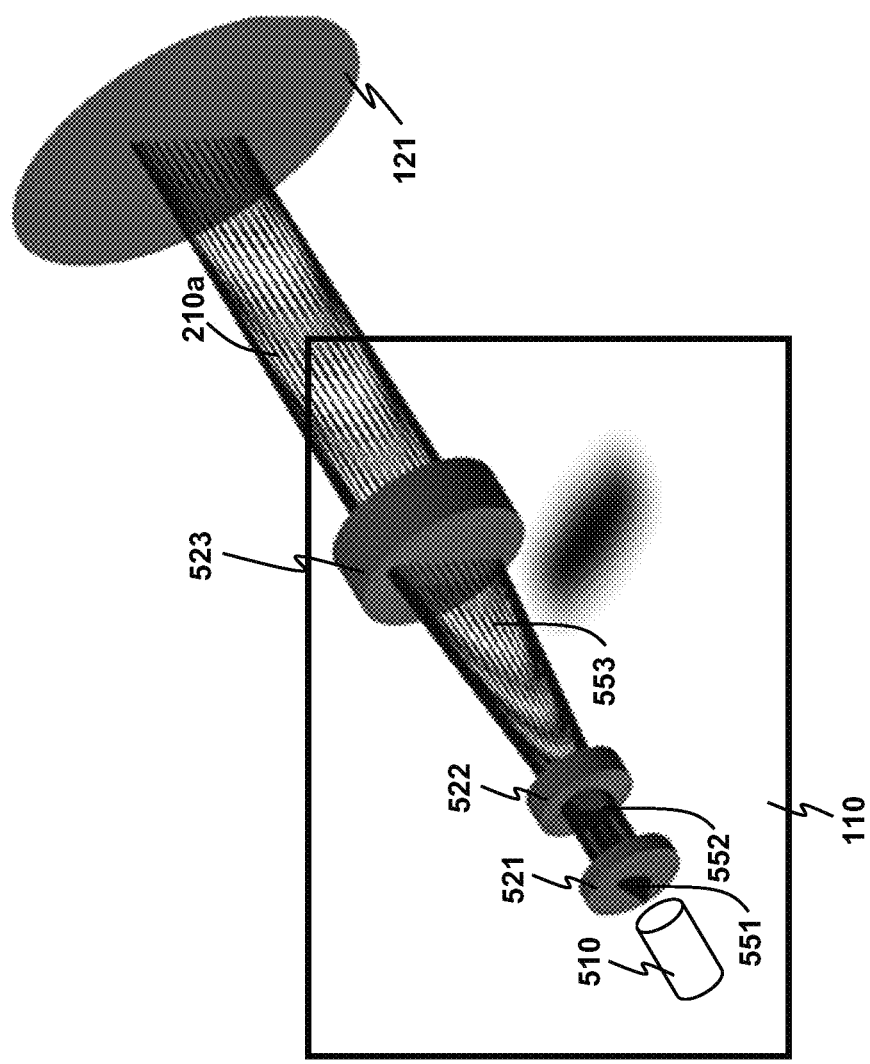
FIG. 6 depicts one embodiment of a line generator for generating a linear light beam with an advantage of using a point source emitting a non-collimated, divergent light beam as a light source for reducing an implementation cost of the disclosed apparatus.
Figure 7:
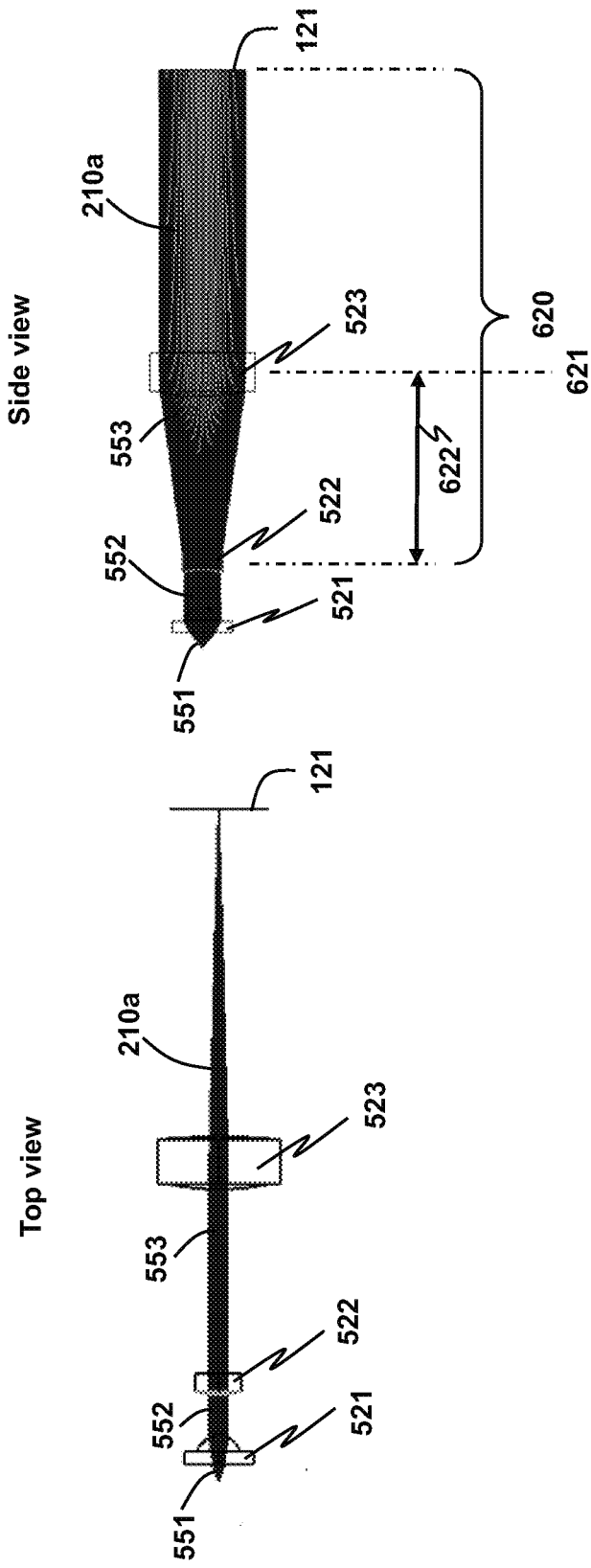
FIG. 7 depicts a top view and a side view of the line generator of FIG. 5.

FIG. 6 depicts one embodiment of the line generator 110 having an advantage that the linear light beam 210a can be generated from a light source that is a point source emitting a non-collimated, divergent light beam. FIG. 7 depicts a top view and a side view of the line generator 110 shown in FIG. 6. By using a point source instead of a light source with high uniformity in power intensity, an implementation cost of the apparatus 100 can be reduced.

In the line generator 110, a light source 510 is used for emitting a raw light beam 551. To reduce an implementation cost of the line generator 110, one may use a point source that provides a divergent cone of light as the light source 510 to provide the raw light beam 551. Note that different light sources are likely to have different angular spreads in respective cones of light, e.g., due to using light sources of different brands or due to random variation in light sources of the same brand.

To remove divergence of the raw light beam 551 as much as possible, a first collimating lens 521 is arranged to receive the raw light beam 551 from the light source 510 and to generate a first collimated light beam 552 from the raw light beam 551. An aspheric lens may be used as the first collimating lens 521. Aspheric lens allows us to provide the best collimation with singe cheap plastic molded optical element.

If the raw light beam 551 is substantially divergent, the cross-sectional length of the first collimated light beam 552 exited from the first collimating lens 521 cannot be set to be a large value; otherwise the first collimated light beam 552 would not be sufficiently collimated. As such, the first collimated light beam 552 may have a short cross-sectional length not long enough as required in realizing the linear light beam 210a (as illustrated in the side view depicted in FIG. 7). A Powell lens 522, also commonly known as a laser line generating lens, is used to fan out the first collimated light beam 552 in one dimension to thereby generate a diverging line 553 of light. The purpose of using the Powell lens 522 is to expand a cross-sectional length of the first collimated light beam 552 as the diverging light line 553 travels, allowing the linear light beam 210a with a required size in cross-sectional length to be obtained from the diverging light line 553.

When the cross-sectional length of the diverging light line 553 reaches the required size of the linear light beam 210a, the diverging light line 553 is received by a first focusing lens 523 for generating the linear light beam 210a. Hence, a cascade of the first collimating lens 521, the Powell lens 522 and the first focusing lens 523 allows the point source to be used as the light source 510 in generating the linear light beam 210a, and enables the first collimating light beam 552 to expand in cross-sectional length for providing a predetermined cross-sectional length required by the linear light beam 210a.

The first focusing lens 523 is positioned at a parking location 621 on a traveling path 620 of the diverging light line 553 and the linear light beam 222a. The parking location 621 is selected such that the cross-sectional length of the diverging light line 553 reaches the predetermined cross-sectional length. In certain embodiments, the parking location 621 is adjustable, providing flexibility in setting the predetermined cross-sectional length required by the linear light beam 210a to be flexible. Adjusting the predetermined cross-sectional length enables a final cross-sectional length of the probe light beam 222e that irradiates the sample 900 to be adaptable to a required scan length in scanning the sample 900. Thus, the flexibility allows samples of different sizes to be scanned by probe light beams of different cross-sectional lengths. In short, a distance 622 between the Powell lens 522 and the first focusing lens 523 is adjustable, allowing the cross-sectional length of the linear light beam 210a to be controllably adjustable for precise alignment and for satisfying practical needs in using the apparatus 100.

The focal length of the first focusing lens 523 is selected to converge the diverging light line 553 such that an angle of divergence of the diverging light line 553 is reduced to zero or to a certain small angle as desired.

In practical realization of the line generator 110, the curvature and aspheric constant of the Powell lens 522 are adjusted such that the diverging light line 533 has a maximally uniform cross-sectional width when the diverging light line 533 is received by the first focusing lens 523 at the parking location 621.

Refer to FIG. 1. A first slit 121 located between the line generator 110 and the beam splitter 120 is advantageously used to make the power intensity of the linear light beam 210 more uniform. In particular, the first slit 121 is configured to filter the linear light beam 210a such that a peripheral region of the linear light beam 210a emitted from the line generator 110 is filtered off, leaving only a central part thereof, which is often more uniform in intensity than the peripheral region. Note that using the linear light beam 210 having a higher uniformity in intensity gives a positive effect of enabling the probe light beam 222e for probing the sample 900 also to have a higher uniformity in intensity. By using the first slit 121, it allows the linear light beam 210b after filtering to be substantially uniform in intensity even if an asymmetrical divergent light source is used as the light source 510, thereby further reducing the manufacturing cost of the apparatus 100 while allowing high-quality accurate measurements of the sample 900 to be achievable.

In realizing the apparatus 100, a reference channel 140 formed by one or more optical components, such as lenses and reflectors, may be used to guide the reference light beam 221 and the returned reference light beam 231 to travel, thereby defining the reference path 171. Specifically, the reference channel 140 is configured to receive the reference light beam 221 exited from the beam splitter 120, allow the reference light beam 221 to travel on a first half of the reference path 171, form the returned reference light beam 231 by reflecting the reference light beam 221, allow the returned reference light beam 231 to travel on a second half of the reference path 171, and direct the returned reference light beam 231 to the beam splitter 120 after traveling on the second half of the reference path 171 is completed. Note that the first and second halves of the reference path 171 have the same optical path length.

Generally, a reference-path mirror 141 is installed at an end of the reference channel 140 for reflecting the reference light beam 221 so as to form the returned reference light beam 231 that travels back to the beam splitter 120.

In OCT, the probe light beam 222e is intended to penetrate into the sample 900. Structural details of a certain selected portion of the sample 900 at a certain depth along an axial direction of the probe light beam 222e are revealed by the probe light beam 222 if the sample path 172 from the beam splitter 120 to this selected portion of the sample 900 is different from the reference path 172 in optical path length by less than a coherence length of the probe light beam 222

(or the linear light beam 210 in practice). The coherence length of the probe light beam 222 can be determined from the coherence time thereof.

Although a length of the reference path 171 may be continuously adjusted in order to probe the sample 900 over a range of depths along the axial direction, this approach, which is employed in time-domain OCT, is time-consuming due to mechanical adjustment of the reference path 171 during depth-scanning of the sample 900. Alternatively, Fourier-domain OCT employs Fourier transform techniques to obtain depth information of the sample 900 at different depths over the range of depths concurrently without a need to mechanically adjusting the length of the reference path 171. Keeping a fixed length of the reference path 171 suffices. As a result, Fourier-domain OCT is faster than time-domain OCT. Details of obtaining the depth information of the sample 900 from the optical interference signal 242 by Fourier-domain OCT can be found in the art, e.g., A. F, FERCHER, W. DREXLER, C. K. HITZENBERGER and T. LASSER, "Optical coherence tomography—principles and applications," *Reports on Progress in Physics*, vol. 66, pp. 239-303, February 2003, the disclosure of which is incorporated by reference herein.

In Fourier-domain OCT, spectral measurement of the optical interference signal 242 is involved in obtaining the tomographical information of the sample 900. It is preferable that a linear spectrometer 160 is used in the apparatus 100 for spectrally measuring the optical interference signal 242 exited from the beam splitter 120 to thereby yield the tomographical information. The linear spectrometer 160 is a spectrometer for an optical signal into spectral components, where a resulting distribution of spectral components on an image plane is linear with respect to the components' wavelengths. As an example, a realization of the linear spectrometer 160 is provided in U.S. Pat. No. 6,650,413.

Preferably and desirably, a second slit 122 is installed in the apparatus 100 and is located between the beam splitter 120 and the linear spectrometer 160 for rejecting unwanted light components from the optical interference signal 242 before the optical interference signal 242 is received by the linear spectrometer 160. The unwanted light components are stray light such as surface reflections from nearby optical components in the apparatus 100.

Figure 8:
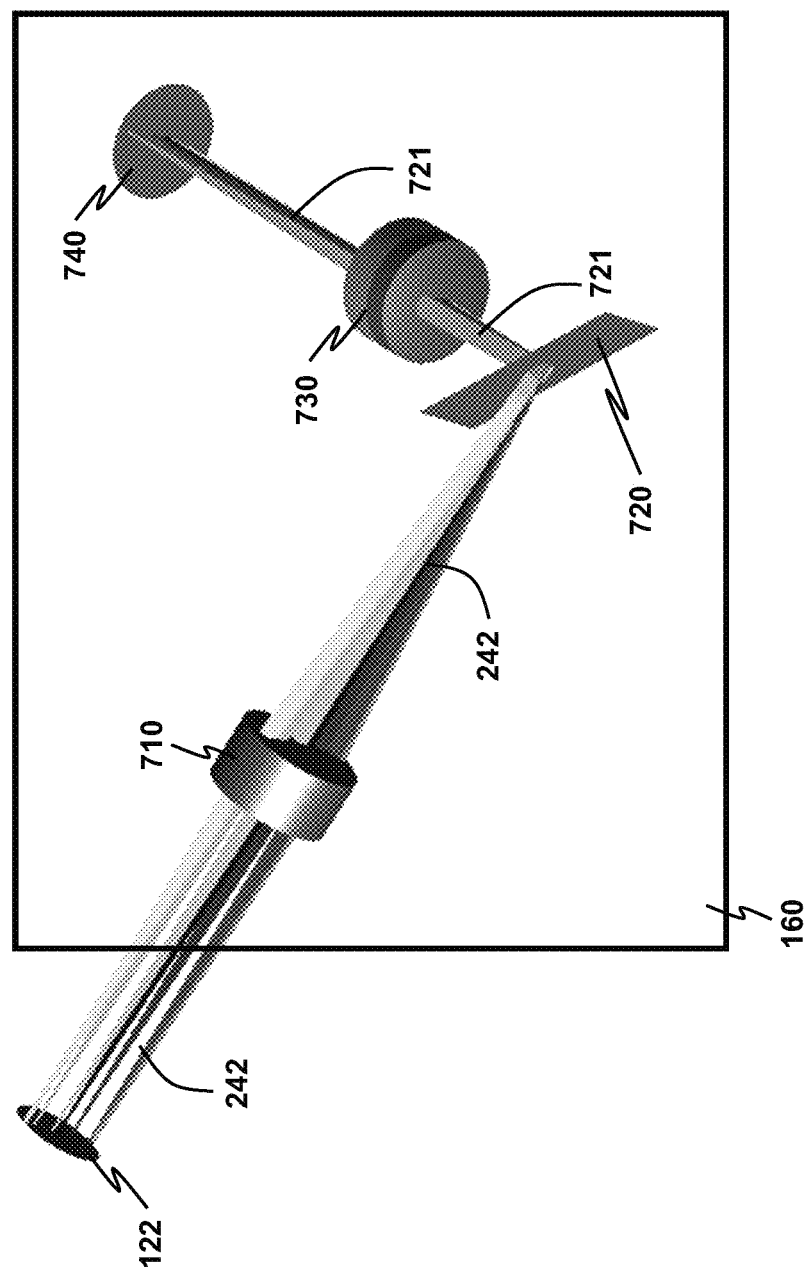
FIG. 8 depicts one embodiment of a linear spectrometer used in the disclosed apparatus for spectrally measuring an optical interference signal.

FIG. 8 depicts one embodiment of the linear spectrometer 160. In the linear spectrometer 160, a second focusing lens 710 receives the optical interference signal 242 from outside the linear spectrometer 160. Furthermore, the second focusing lens 710 projects the optical interference signal 242 to a diffraction grating 720. The diffraction grating 720 diffracts the optical interference signal 242 to form a diffraction pattern (herein referred to as a spectral image 721) so as to disperse the optical interference signal 242 into spectra, where the spectral image 721 contains a distribution of dispersed spectra. The spectral image 721 is projected onto a 2D photosensor 740 such that the spectral image 721 is imaged to obtain the distribution of dispersed spectra. In the linear spectrometer 160, a third focusing lens 730 positioned between the diffraction grating 720 and the 2D photosensor 740 projects the spectral image 721 onto the 2D photosensor 740.

Other implementation details of the apparatus 100 are elaborated as follows.

Since the mirror 130 can be advantageously miniaturized as explained above, the mirror 130 may be realized as a MEMS mirror. The MEMS mirror is a MEMS allowing a high degree of integration of a small reflecting mirror, an actuator for driving the reflecting mirror, and an electronic controller for controlling the actuator.

The beam splitter 120 may be realized as a cube beam splitter. Alternatively, the beam splitter 120 may also be realized as a plate beam splitter. Other realizations of the beam splitter 120 are possible.

As mentioned above, the optical path length of the reference path 171 may be kept constant in Fourier-domain OCT during depth-scanning the sample 900. Despite this, it is sometimes possible to obtain some performance improvement in extracting spectral information from the optical interference signal 242 by fine-tuning the optical path length of the reference path 171. Optionally, an actuator 142, e.g., a piezoelectric actuator, is attached to the reference-path mirror 141 for adjusting the optical path length of the reference path 171. If the piezoelectric actuator is operated in the ultrasonic range, adjusting the optical path length of the reference path 171 is inaudible, avoiding distraction to an operator of the apparatus 100 or a person doing retinal imaging by the apparatus 100.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. An apparatus for imaging a sample by optical coherence tomography (OCT), the apparatus comprising:
    a line generator for generating a linear light beam;
    a beam splitter configured to split the linear light beam into a reference light beam and a probe light beam, the probe light beam being arranged to travel from the beam splitter to the sample over a sample path for line-scanning the sample to thereby cause the sample to generate a backscattered light beam, the sample path allowing the backscattered light beam to be transmitted to the beam splitter, the reference light beam being arranged to travel along a reference path and return to the beam splitter, the beam splitter being further configured to combine the returned reference light beam and the backscattered light beam to form an optical interference signal for analysis to thereby yield tomographical information of the sample;
    a telescope on the sample path, the telescope being configured to project the probe light beam to the sample and capture the backscattered light beam;
    a mirror on the sample path for reflecting the probe light beam exited from the beam splitter to the telescope and reflecting the backscattered light beam exited from the telescope to the beam splitter, wherein the mirror is controllably steerable so as to steer the probe light beam to different parts of the sample in line-scanning the sample; and
    a line-compression lens on the sample path between the beam splitter and the mirror, wherein the line-compression lens is configured to compress a cross-sectional length of the probe light beam from a first length to a shorter, second length when the probe light beam reaches the mirror, the probe light beam at the line-compression lens having a cross-sectional width shorter than the cross-sectional length, and wherein the second length defines a size of the mirror such that the mirror has a reduced size sufficient to accommodate the probe light beam having the second length in cross-sectional length instead of a larger size required to accommodate the probe light beam having the first length in cross-sectional length, thereby allowing the mirror to be miniaturized.

2. The apparatus of claim 1, wherein the line-compression lens is further configured to keep the cross-sectional width of the probe light beam substantially unchanged over the sample path between the line-compression lens and the mirror.

3. The apparatus of claim 1, wherein the line generator comprises:
a light source for emitting a raw light beam;
a first collimating lens for generating a first collimated light beam from the raw light beam;
a Powell lens for generating a diverging line of light from the first collimated light beam; and
a first focusing lens for generating the linear light beam from the diverging light line, whereby a cascade of the first collimating lens, the Powell lens and the first focusing lens allows a point source to be used as the light source in generating the linear light beam, and enables the first collimating light beam to expand in cross-sectional length for providing a predetermined cross-sectional length required by the linear light beam.

4. The apparatus of claim 3, wherein a distance between the Powell lens and the first focusing lens is adjustable, allowing a cross-sectional length of the linear light beam to be controllably adjustable.

5. The apparatus of claim 3 further comprising:
a first slit located between the line generator and the beam splitter for filtering the linear light beam before reaching the beam splitter such that a peripheral portion of the linear light beam emitted from the line generator is filtered off, thereby allowing the linear light beam after filtering to be substantially uniform in intensity even if an asymmetrical divergent light source is used as the light source.

6. The apparatus of claim 1, wherein the linear light beam is infrared.

7. The apparatus of claim 1, wherein the mirror is a microelectromechanical system (MEMS) mirror.

8. The apparatus of claim 1 further comprising:
a reference channel configured to receive the reference light beam exited from the beam splitter, allow the reference light beam to travel on a first half of the reference path, form the returned reference light beam by reflecting the reference light beam, allow the returned reference light beam to travel on a second half of the reference path, and direct the returned reference light beam to the beam splitter after traveling on the second half of the reference path is completed.

9. The apparatus of claim 8 further comprising:
a reference-path mirror installed at an end of the reference channel for reflecting the reference light beam so as to form the returned reference light beam that travels back to the beam splitter.

10. The apparatus of claim 9 further comprising:
an actuator attached to the reference-path mirror for fine-tuning an optical path length of the reference path.

11. The apparatus of claim 10, wherein the actuator is a piezoelectric actuator.

12. The apparatus of claim 1 further comprising:
a linear spectrometer for spectrally measuring the optical interference signal to thereby yield the tomographical information of the sample.

13. The apparatus of claim 12 further comprising:
a second slit located between the beam splitter and the linear spectrometer for rejecting unwanted light components from the optical interference signal before the optical interference signal is received by the linear spectrometer.

14. The apparatus of claim 12, wherein the linear spectrometer comprises:
a diffraction grating for diffracting the optical interference signal so as to disperse the optical interference signal into spectra to thereby form a spectral image, the spectral image containing a distribution of dispersed spectra;
a second focusing lens for receiving the optical interference signal from outside the linear spectrometer and projecting the received optical interference signal to the diffraction grating;
a two-dimensional (2D) photosensor for imaging the spectral image to obtain the distribution of dispersed spectra; and
a third focusing lens positioned between the diffraction grating and the 2D photosensor for projecting the spectral image onto the 2D photosensor.

15. The apparatus of claim 1, wherein the beam splitter is a cube beam splitter or a plate beam splitter.

16. The apparatus of claim 1, wherein the telescope comprises a first telescope lens and a second telescope lens arranged in a serial cascade.

17. The apparatus of claim 16, wherein the first telescope lens, the second telescope lens, or both, are adjustable in optical power for accurately projecting the probe light beam on the sample.

* * * * *